US005245074A

United States Patent [19]

Shah et al.

[11] Patent Number: 5,245,074

[45] Date of Patent: Sep. 14, 1993

[54] PROCESS FOR THE PRODUCTION OF 4-ACETOXYSTYRENE, ITS POLYMERS AND HYDROLYSIS PRODUCTS

[76] Inventors: Bakulesh N. Shah, 5510 Fox Run Dr., Corpus Christi, Tex. 78413; Dung Q. Tran, 23 Sedgefield Rd., North Kingstown, R.I. 02852; Donna L. Keene, Rte. 1, Box 215, Carrollton, Va. 23314

[21] Appl. No.: 886,990

[22] Filed: May 21, 1992

Related U.S. Application Data

[60] Division of Ser. No. 598,510, Oct. 15, 1990, Pat. No. 5,151,546, which is a continuation-in-part of Ser. No. 425,399, Oct. 17, 1989, abandoned, which is a continuation of Ser. No. 221,146, Jul. 19, 1988, abandoned, which is a continuation-in-part of Ser. No. 221,145, Jul. 19, 1988, abandoned.

[51] Int. Cl.[5] .......... C07C 67/297

[52] U.S. Cl. .......... 560/130; 560/239

[58] Field of Search .......... 560/130, 239

[56] References Cited

U.S. PATENT DOCUMENTS

| | | | |
|---|---|---|---|
| 2,628,985 | 2/1953 | Winkler . | |
| 2,739,961 | 3/1956 | Drew et al. . | |
| 3,014,958 | 12/1961 | Koch et al. . | |
| 3,607,719 | 9/1971 | Johnson et al. | 208/8 |
| 3,859,311 | 1/1975 | Symon et al. . | |
| 4,129,557 | 12/1978 | Kudo et al. | 525/283 |
| 4,316,995 | 2/1982 | Pittet et al. | 568/780 |
| 4,689,371 | 8/1987 | Elmore et al. | 525/374 |
| 4,783,503 | 11/1988 | Gergen et al. | 525/66 |

FOREIGN PATENT DOCUMENTS

| | | |
|---|---|---|
| 61-204147 | 10/1986 | Japan . |
| 872192 | 7/1961 | United Kingdom . |

OTHER PUBLICATIONS

Corson, et al, "Preparation of Vinylphenols and Isopropenylphenols", J. Org. Chem, Sep. 1957.

*Primary Examiner*—Joseph L. Schofer
*Assistant Examiner*—Jeffrey T. Smith

[57] ABSTRACT

A method for producing 4-acetoxystyrene by heating 4-acetoxyphenylmethylcarbinol, with an acid catalyst, at a temperature of from about 85° C. to about 300° C. under a pressure of from about 0.1 mm HgA to about 760 mm HgA for from about 0.2 minutes to about 10 minutes. The process also provides for the solventless (neat) hydrogenation of 4-acetoxyacetophenone to produce 4-acetoxyphenylmethylcarbinol. The reaction proceeds by heating at 54° C. to 120° C. with an excess of hydrogen in the presence of a Pd/C or activated nickel such as Raney Nickel catalyst in the absence of a solvent. The 4-acetoxyphenylmethylcarbinol may then be dehydrated to 4-acetoxystyrene. The later may be polymerized to poly(4-acetoxystyrene) and hydrolyzed to poly(4-hydroxystyrene).

12 Claims, No Drawings

PROCESS FOR THE PRODUCTION OF 4-ACETOXYSTYRENE, ITS POLYMERS AND HYDROLYSIS PRODUCTS

This is a division of co-pending application Ser. No. 07/598,510 filed on Oct. 15, 1990 now U.S. Pat. No. 5,151,546, which was a continuation-in-part of U.S. patent application Ser. No. 07/425,399 filed Oct. 17, 1989 now abandoned, which was a continuation of U.S. patent application Ser. No. 07/221,146 filed Jul. 19, 1988 now abandoned and which was a continuation-in-part of U.S. patent application Ser. No. 07/221,145 filed Jul. 19, 1988, now abandoned.

BACKGROUND OF THE INVENTION

The present invention relates to a process for the solventless hydrogenation of 4-acetoxyacetophenone and to a process for the low residence time dehydration of 4-acetoxyphenylmethylcarbinol. These processes are useful in improved methods for the production of 4-acetoxystyrene, poly(4-acetoxystyrene) homopolymers, copolymers and terpolymers with 4-acetoxystyrene as one of the monomers, and the hydrolysis of poly(4-acetoxystyrene) to poly(4-hyrdoxystyrene), including hydrolysis of copolymers and terpolymers containing 4-acetoxystyrene.

It is known in the art to produce monomers, homopolymers and copolymers of 4-acetoxystyrene and to hydrolyze the same to produce 4-hydroxystyrene derivatives or poly(4-hydroxystyrene). These compounds may be employed in the production of adhesives, coating compositions, and the like. Poly(4-hydroxystyrene) compounds are useful as binder resins for photoresists. Alpha acetoxystyrene and beta acetoxystyrene are known compounds and are described in U.S. Pat. No. 4,144,063 and acetoxymethylstyrene is described in U.S. Pat. No. 3,963,495. U.S. Pat. No. 4,075,237 describes 1,4-dimethyl-2-hydroxystyrene, while U.S. Pat. No. 4,565,846 teaches the use of poly(3,5-dimethyl-4-hydroxystyrene). Japanese patent 84023747 describes anti-static compounds employing poly(acetoxymethylstyrene) and U.S. Pat. No. 4,221,700 describes a stabilized synthetic polymer composition using poly(alkylated alkenylphenol) including 2-methyl paravinyl phenol. U.S. Pat. Nos. 4,600,683 and 4,543,397 describe poly(alphamethyl vinylphenol). U.S. Pat. Nos. 4,517,028; 4,460,770 and 4,539,051 describe dimethylvinylphenol.

The preparation of 4-hydroxystyrene is well known in the art. One process is described in U.S. Pat. No. 4,316,995 and another is described in U.S. Pat. No. 4,451,676. Vinyl phenol may be prepared by a five step process of (1) acetylating phenol to p-hydroxyacetophenone, (2) acetylation of p-hydroxyacetophenone to p-acetoxyacetophenone, (3) hydrogenation of p-acetoxyacetophenone to p-acetoxyphenylmethylcarbinol, (4) dehydration of p-acetoxyphenylmethylcarbinol to p-acetoxystyrene, and (5) saponification of p-acetoxystyrene to p-vinylphenol. This latter method is more fully described in Corson, B. B., et al, *Preparation of Vinvlphenols and Isooropenvlphenols*, J. Org. Chem., Apr. 1958.

Known processes for the hydrogenation of 4-acetoxyacetophenone to 4-acetoxyphenylmethylcarbinol have been conducted with a Pd/C catalyst. This method has required the presence of such solvents as methanol and tetrahydrofuran. While this hydrogenation may be used in conjunction with the special dehydration process of this invention, it is a lesser preferred embodiment since the use of the solvent necessarily requires its ultimate removal. Problems which have been experienced include the dissolution of the 4-acetoxyacetophenone in the solvent; increased reactor volume due to the presence of the solvent; subsequent removal of the Pd/C catalyst from the large volume of solvent in the 4-acetoxyphenylmethylcarbinol mixture; separation of the solvent from 4-acetoxyphenylmethylcarbinol; purification and recycling of the solvent; solvent losses; and by-products from the solvent. The present invention most preferably employs a process wherein the solvent is completely eliminated. By this means it has been found that the selectivity of the reaction is substantially not adversely affected by the elimination of the solvent component. Also, other side reactions are not observed and an economical operation of the process is made possible.

This invention especially provides an improved method for dehydrating 4-acetoxyphenylmethylcarbinol. This is performed by heating at 85° C. to 300° C. under a vacuum of about 0.1 mm HgA to 760 mm HgA, preferably for about ten minutes or less and more preferably about two minutes or less in the presence of an acid catalyst. Conventional practice conducts this reaction in a batch reactor. Unfortunately, the batch process required about three hours. The present invention substantially improves (reduces) reaction time by employing a low residence time reaction. In addition, a reaction selectivity increase of at least about 10% is observed. In other words, the 4-acetoxyphenylmethylcarbinol is exposed to high temperatures for relatively short time periods for conversion into 4-acetoxystyrene, with a resultant improvement in the selectivity to 4-acetoxystyrene of at least 10% being obtained.

SUMMARY OF THE INVENTION

The invention provides a method for producing 4-acetoxystyrene which comprises heating 4-acetoxyphenylmethylcarbinol in the presence of a catalytic amount of an acid, at a temperature of from about 85° C. to 300° C. under a pressure of from about 0.1 mm HgA to about 760 mm HgA for a period of time of from about 0.2 minutes to about 10 minutes.

The invention also provides a process for the production of 4-acetoxystyrene which comprises:

a) acylating phenol with acetic anhydride to produce 4-hydroxyacetophenone; and
b) acylating the 4-hydroxyacetophenone with acetic anhydride to form 4-acetoxyacetophenone; and
c) hydrogenating 4-acetoxyacetophenone to produce 4-acetoxyphenylmethylcarbinol. This is most preferably performed by heating 4-acetoxyacetophenone at a temperature of from about 54° C. to about 120° C. in the presence of at least a stoichiometric amount of hydrogen, and a catalytic amount of a catalyst selected from the group consisting of Pd/C or activated nickel such as Raney Nickel in the absence of a solvent, for a sufficient time to produce 4-acetoxyphenylmethylcarbinol; and
d) heating 4-acetoxyphenylmethylcarbinol, in the presence of a catalytic amount of an acid catalyst, at a temperature of from about 85° C. to 300° C. under a pressure of from about 0.1 mm HgA to about 760 mm HgA for a period of time of from about 0.2 minutes to about 10 minutes.

The invention also provides a process for the production of poly(4-acetoxystyrene) which comprises subsequent free radical polymerization of the 4-acetoxystyrene to form poly(4-acetoxystyrene) having a molecular weight in the range of from about 1,000 to about 800,000, preferably about 5,000 to about 500,000.

The invention still further provides a process for the production of poly(4-hydroxystyrene) which comprises subsequently hydrolyzing the poly(4-acetoxystyrene) to form poly(4-hydroxystyrene) having a molecular weight in the range of from about 1,000 to about 500,000, preferably about 5,000 to about 500,000.

The invention further provides a method for producing 4-acetoxyphenylmethylcarbinol which comprises heating 4-acetoxyacetophenone at a temperature of from about 54° C. to about 120° C. in the presence of at least a stoichiometric amount of hydrogen, and a catalyst selected from the group consisting of Pd/C or activated nickel such as Raney Nickel in the absence of a solvent, for a sufficient time to produce 4-acetoxyphenylmethylcarbinol.

The invention still further provides a process for the production of 4-acetoxystyrene which comprises:

a) acylating phenol with acetic anhydride to produce 4-hydroxyacetophenone; and
b) acylating the 4-hydroxyacetophenone with acetic anhydride to form 4-acetoxyacetophenone; and
c) heating 4-acetoxyacetophenone at a temperature of from about 54° C. to about 120° C. in the presence of at least a stoichiometric amount of hydrogen, and a catalyst selected from the group consisting of Pd/C or activated nickel such as Raney Nickel in the absence of a solvent, for a sufficient time to produce 4-acetoxyphenylmethylcarbinol; and
d) dehydrating the 4-acetoxyphenylmethylcarbinol to produce 4-acetoxystyrene.

The invention also provides a process for the production of poly(4-acetoxystyrene) which comprises subsequent free radical polymerization of the 4-acetoxystyrene to form poly(4-acetoxystyrene) having a molecular weight in the range of from about 1,000 to about 800,000, preferably about 5,000 to about 500,000.

The invention still further provides a process for the production of poly(4-hydroxystyrene) which comprises subsequently hydrolyzing the poly(4-acetoxystyrene) to form poly(4-hydroxystyrene) having a molecular weight in the range of from about 1,000 to about 500,000, preferably about 5,000 to about 500,000.

DETAILED DESCRIPTION OF THE PREFERRED EMBODIMENT

In the process for the production of 4-acetoxystyrene, one begins with phenol and acylates it with acetic anhydride via a Friedel-Crafts catalysis or Fries rearrangement to produce 4-hydroxyacetophenone. This 4-hydroxyacetophenone is then acetylated with acetic anhydride to form 4-acetoxyacetophenone. The latter is then hydrogenated, preferably neat hydrogenated without a solvent to form 4-acetoxyphenylmethylcarbinol. This is then dehydrated, preferably low residence time dehydrated, with an acid or base to form 4-acetoxystyrene monomer. Free radical polymerization and hydrolysis may follow.

A typical overall reaction sequence may be described schematically as follows:

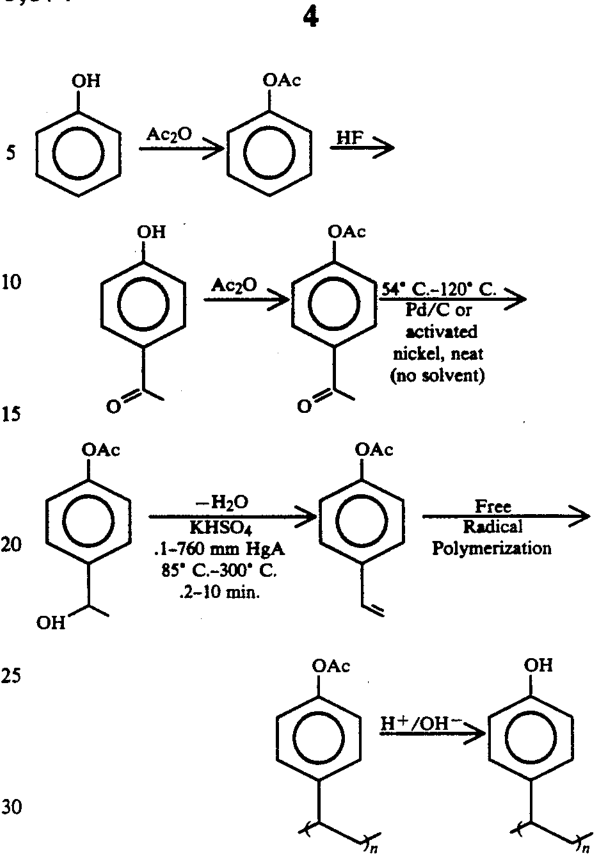

In the preferred embodiment the first reaction steps proceed as follows. One charges a reaction vessel with phenol and a slight excess of acetic anhydride to form phenylacetate. The phenylacetate is then subjected to a Friedel-Crafts catalyst such as hydrogen fluoride to form 4-hydroxyacetophenone. This last reaction is conducted at a temperature of from about 5° C. to about 100° C., or more preferably from about 20° C. to about 80° C. A most preferred temperature is about 50° C. The reaction proceeds at a preferred pressure of from about 700 mm Hg to about 780 mm Hg for from about 1 to about 5 hours. Although hydrogen fluoride is the preferred catalyst, other Lewis acids may be also used such as $AlCl_3$, $BF_3$, $HClO_4$, $FeCl_3$ and $SnCl_4$. The Fries rearrangement may be conducted in a manner well known to the skilled artisan. The reaction product is 4-hydroxyacetophenone. This 4-hydroxyacetophenone is then acetylated with acetic anhydride. In this process, the 4-hydroxyacetophenone is refluxed with an excess of acetic anhydride for from about 2 to about 6 hours. Excess acetic anhydride as well as generated acetic acid are removed by distillation in vacuo. This is conducted, for example at a pressure of from about 0.1 to about 1,000 mm Hg and at an initial temperature of from about 135° C. to about 150° C., preferably from about 135° C. to about 145° C. which is then reduced to from about 35° C. to about 85° C.

The 4-acetoxyacetophenone is then hydrogenated, preferably neat hydrogenated without the use of a solvent to form 4-acetoxyphenylmethylcarbinol. This is performed by heating 4-acetoxyacetophenone at a temperature of from about 54° C. to about 120° C. in the presence of at least a stoichiometric amount of hydrogen, and a catalyst selected from the group consisting of Pd/C or activated nickel such as Raney Nickel in the absence of a solvent, for a sufficient time to produce 4-acetoxyphenylmethylcarbinol. In the more preferred embodiment, the reaction is conducted at a temperature of from about 60° C. to about 90° C. In the preferred embodiment, the reaction is conducted until substantial completion of hydrogenation as indicated by a lack of $H_2$ uptake, normally about 2 to 7 hours. In the preferred embodiment, when Pd/C is used, the reaction proceeds at a pressure of from about 14.7 psig to about 5,000 psig, more preferably at a pressure of from abut 50 psig to about 500 psig and most preferably at a pressure of from about 100 psig to about 400 psig. When activated nickel is used the reaction proceeds at a pressure of from about 14.7 to about 5,000 psig, more preferably from about 300 to about 680 psig and most preferably from about 350 to about 450 psig. Activated nickel is the preferred catalyst since it can be recycled and a process with a higher selectivity is attained. In another embodiment, although lesser preferred, the 4-acetoxyacetophenone is hydrogenated with a suitable reagent to form the 4-acetoxyphenylmethylcarbinol. One preferred reagent is $NaBH_4$. Other reagents non-exclusively include lithium aluminum hydride, hydrogen, and diisobutyl aluminum hydride. Solvents such as ethanol, methanol or tetrahydrofuran may be used in combination with the preceeding reagents. Other methods of hydrogenation are discussed in Corson, above, at page 548, which is incorporated herein by reference.

This product is then dehydrated. Several prior known batch dehydration methods are taught by Corson. Dehydration is preferably conducted by vacuum heating in the presence of a polymerization inhibitor and a dehydrating agent. In one preferred embodiment, the 4-acetoxyphenylmethylcarbinol is mixed with a $KHSO_4$ dehydrating agent and t-butyl catechol as a polymerization inhibitor. Other useful dehydrating agents non-exclusively include alumina, titania, silica gel and mineral acids. Other polymerization inhibitors non-exclusively include hydroquinone, tetrachloroquinone, tert-butyl catechol, phenothiazine, and di-t-butyl-p-cresol. The dehydrating agent is present in an amount of from about 0.25 to about 5.0 percent by weight of the 4-acetoxyphenylmethylcarbinol.

The polymerization inhibitor is preferably present in an amount of from about 1% to about 5% based on the weight of the 4-acetoxyphenylmethylcarbinol. In one embodiment of the invention, the dehydration is conducted in a low residence time apparatus such as a thin film evaporator, the output of which connects to a distillation column. In this particular case, the 4-acetoxyphenylmethylcarbinol, catalyst and polymerization inhibitor may be metered into the evaporator or the distillation column at a rate sufficient to achieve the desired residence time. With this method, a thin film of the carbinol mixture is constantly wiped by a wiper rotating in the evaporator. The evaporator may be heated with hot oil or steam. The reaction vessel is heated to from about 85° C. to about 300° C., preferably 170° C. to about 250° C. at a pressure of from about 0.1 mm HgA to about 760 mm Hg, preferably from about 0.5 mm HgA to about 250 mm HgA. The residence time of the mixture in the evaporator ranges from about 0.2 minutes to about 10 minutes, preferably about 2 minutes or less. Thin film evaporators are per se well known in the art and need not be more fully described here. At the exit end of the evaporator, a distillation column is attached. The reaction product contains 4-acetoxystyrene, water, and some unreacted 4-acetoxyphenylmethylcarbinol. The 4-acetoxystyrene and water are collected in the overhead of the distillation column. Tar is collected as a liquid at the exit end of the evaporator. Unreacted 4-acetoxyphenylmethylcarbinol goes back down the distillation column and re-enters the evaporator. The resultant product is 4-acetoxystyrene which is obtained at a selectivity rate of at least from about 70% to about 95%. Although a thin film evaporator is one tool which may be used for conducting the dehydration process, it is not critical to the practice of the invention. Any means for attaining the low residence dehydration is within the scope of the invention provided the residence time of the mixture ranges from about 0.2 minutes to about 10 minutes, preferably about 2 minutes or less.

The 4-acetoxystyrene monomer may then be polymerized by a free radical initiation process to produce poly(4-acetoxystyrene) such that it has a molecular weight in the range of from about 1,000 to about 800,000, preferably 5,000 to 500,000 or more preferably about 5,000 to about 300,000. This intermediate is then hydrolyzed with a base or acid to form poly(4-hydroxystyrene) such that it also has the aforesaid molecular weight range. One preferred free radical initiator is azoisobutyronitrile. Other azo type initiators are also suitable. Still others nonexclusively include peroxides such as benzoyl peroxide, and di-t-butyl peroxide. It is predicted that essentially any free radical initiation system will serve in the same fashion. One preferred hydrolyzing agent is tetramethylammonium hydroxide. Other hydrolyzing agents non-exclusively include aqueous $NH_3$, NaOH, KOH, HCl, and $H_2SO_4$.

The following non-limiting examples serve to illustrate the invention.

EXAMPLE 1

In a glass thin film evaporator, 4-acetoxyphenylmethylcarbinol containing 1% by weight of $KHSO_4$ and 1% by weight of 4-tert-butyl catechol are fed at a rate of 3.2 g/min. The thin film evaporator is heated to 240° C. and the pressure is 242 mm HgA. The total feed is 45.1 g and contains 83.3% 4-acetoxyphenylmethylcarbinol by weight. The total overhead collected is 38.1 g. The analysis of the overhead by gas chromatography is 67.5% 4-acetoxystyrene, 11.4% 4-acetoxyphenylmethylcarbinol and the balance is due to other components. The 4-acetoxyphenylmethylcarbinol conversion is 88.4% and the selectivity to 4-acetoxystyrene is 86%.

EXAMPLE 2

In a glass thin film evaporator, 4-acetoxyphenylmethylcarbinol containing 1% by weight of $KHSO_4$ and 1% by weight of 4-tert-butyl catechol are fed at a rate of 3.2 g/min. The thin film evaporator is heated to 220° C. and the pressure is 157 mm HgA. The total feed is 45.6 g and contains 83.3% 4-acetoxyphenylmethylcarbinol by weight. The total overhead collected is 36.5 g. The analysis of the overhead by gas chromatography is 64.1% 4-acetoxystyrene, 15.8% 4-acetoxyphenylmethylcarbinol and the balance is due to other components. The 4-acetoxyphenylmethylcarbinol conversion is 84.9% and the selectivity to 4-acetoxystyrene is 80.7%.

EXAMPLE 3

In a glass thin film evaporator, 4-acetoxyphenylmethylcarbinol containing 2% by weight of $KHSO_4$ and 1% by weight of 4-tert-butyl catechol are fed at a rate of 1.9 g/min. The thin film evaporator is heated to 240° C. and the pressure is 155 mm HgA. The total feed is 250 g and contains 83.3% 4-acetoxyphenylmethylcarbinol by weight. The total overhead collected is 216.2 g. The analysis of the overhead by gas chromatography is 68.0% 4-acetoxystyrene, 8.7% 4-acetoxyphenylmethylcarbinol and the balance is due to other components. The 4-acetoxyphenylmethylcarbinol conversion is 91.0% and the selectivity to 4-acetoxystyrene is 86.3%.

EXAMPLE 4

In a glass thin film evaporator, 4-acetoxyphenylmethylcarbinol containing 5% by weight of $KHSO_4$ and 2% by weight of 4-tert-butyl catechol are fed at a rate of 1.6 g/min. The thin film evaporator is heated to 240° C. and the pressure is 155 mm HgA. The total feed is 400 g and contains 59.7% 4-acetoxyphenylmethylcarbinol by weight. The total overhead collected is 295 g. The analysis of the overhead by gas chromatography is 62.3% 4-acetoxystyrene, 11.4% 4-acetoxyphenylmethylcarbinol and the balance is due to other components. The 4-acetoxyphenylmethylcarbinol conversion is 87.9 and the selectivity to 4-acetoxystyrene is 84.4%.

EXAMPLE 5

In a glass thin film evaporator, 4-acetoxyphenylmethylcarbinol containing 1% by weight of $KHSO_4$ and 1% by weight of 4-tert-butyl catechol are fed at a rate of 11.2 g/min. The thin film evaporator is heated to 240° C. and the pressure is 155 mm HgA. The total feed is 78.1 g and contains 83.3% 4-acetoxyphenylmethylcarbinol by weight. The total overhead collected is 74.1 g. The analysis of the overhead by gas chromatography is 68.7% 4-acetoxystyrene, 9.5% 4-acetoxyphenylmethylcarbinol and the balance is due to other components. The 4-acetoxyphenylmethylcarbinol conversion is 89.1% and the selectivity to 4-acetoxystyrene is 97.5%.

EXAMPLE 6

In a glass thin film evaporator, 4-acetoxyphenylmethylcarbinol containing 1% by weight of $KHSO_4$ and 1% by weight of 4-tert-butyl catechol are fed at a rate of 1.8 g/min. The thin film evaporator is heated to 240° C. and the pressure is 155 mm HgA. The total feed is 55.8 g and contains 83.3% 4-acetoxyphenylmethylcarbinol by weight. The total overhead collected is 46.5 g. The analysis of the overhead by gas chromatography is 68.0% 4-acetoxystyrene, 8.7% 4-acetoxyphenylmethylcarbinol and the balance is due to other components. The 4-acetoxyphenylmethylcarbinol conversion is 91.3% and the selectivity to 4-acetoxystyrene is 82.8%.

EXAMPLE 7

75 grams of 4-acetoxyacetophenone and 7.5 g of Pd/C catalyst (5% Pd carbon) are charged in a 300-ml stirred reactor. The reactor is pressure checked with nitrogen at 150 psig. The nitrogen is then purged twice with 100 psig hydrogen. The hydrogen pressure is maintained at 100 psig. The reactor is then heated to 60° C. to carry out the reaction. After three hours of reaction time, the reaction is stopped by venting off hydrogen. A sample of the reaction mass is analyzed by gas chromatography. The analysis shows 4-acetoxyphenylmethylcarbinol 77.4%, unreacted 4-acetoxyacetophenone 6.6%, 4-ethylphenol 1.5%, 4-ethylphenyl acetate 0.2% and the balance is as due to other components.

EXAMPLE 8

12 kg of 4-acetoxyacetophenone and 450 g of Pd/C catalyst (5% Pd on carbon) are charged in a 5-gal stirred reactor. The 4-acetoxyacetophenone is melted before charging in the reactor. After pressure testing with nitrogen, the reactor is charged with hydrogen at 100 psig and the reactor contents are heated to 60° C. After 8 hours, the heat is turned off to stop the reaction. The product analysis by gas chromatography gives 92.3% 4-acetoxyphenylmethylcarbinol, 1.8% 4-ethylphenyl acetate, 0.3% 4-acetoxyacetophenone, 1.6% ethylbenzene and the balance is due to other components.

EXAMPLE 9

12 kg of 4-acetoxyacetophenone and 450 g of Pd/C catalyst (5% Pd on carbon) are charged in a 5-gal stirred reactor. The reactor is then charged with hydrogen at 80 psig and the reactor contents are then heated to 60° C. After 8 hours of reaction time, the reaction is stopped. The product analysis by gas chromatography gives 94% 4-acetoxyphenylmethylcarbinol, 1.3% ethylphenol, 1.2% 4-ethylphenyl acetate, 2.5% 4-acetoxyacetophenone and the balance is due to other components.

EXAMPLE 10

102 g of 4-acetoxyacetophenone and 10 g of Raney nickel catalyst are charged in a 300-ml stirred reactor. The reactor is then charged with hydrogen at 500 psig and heated to 60° C. for 270 minutes. The reactor is then cooled down and the product analyzed by gas chromatography. The analysis gives 80.4% 4-acetoxyphenylmethylcarbinol.

EXAMPLE 11

99.8 g of 4.acetoxyacetophenone and 4 g of Pd/C catalyst (5% Pd on carbon) are charged in a 300-ml stirred reactor. The reactor is then charged with hydrogen at 100 psig. The contents are heated to 60° C. After 4.25 hours, the reactor is cooled down and the product is analyzed by ga chromatography. The analysis is 94% of 4-acetoxyphenylmethylcarbinol, 2% ethylbenzene, 0.7% 4-ethylphenyl acetate and the balance is due to other components.

EXAMPLE 12

10 kg of melted 4-acetoxyacetophenone and 1.1 kg of Raney nickel catalyst are charged in a 20-1 stirred reactor. The contents are heated to 60° C. at 400 psig of nitrogen. The reactor is then charged with hydrogen. After 4 hours, the reactor is cooled down and the liquid product is analyzed by gas chromatography. The analysis is 97% acetoxyphenylmethylcarbinol, 0.1% ethylbenzene, 0.2% ethylphenyl acetate, 1.3% 4-acetoxyacetophenone and the balance is due to other components.

What is claimed is:

1. A process for the production of 4-acetoxystyrene which comprises:

a) acylating phenol with acetic anhydride to produce 4-hydroxyacetophenone; and b) acylating the 4-hydroxyacetophenone with acetic anhydride to form 4-acetoxyacetophenone; and c) heating 4-acetoxyacetophenone at a temperature of from about 54° C. to about 120° C. in the presence of at least a stoichiometric amount of hydrogen, and a catalytic amount of a catalyst selected from the group consisting of Pd/C or activated nickel in the absence of a solvent, for a sufficient time to produce 4-acetoxyphenylmethylcarbinol; and d) heating 4-acetoxyphenylmethylcarbinol, in the presence of a catalytic amount of an acid catalyst, at a temperature of from about 85° C. to 300° C. under a pressure of from about 0.1 mm HgA to about 760 mm HgA for a period of time of from about 0.2 minutes to about 10 minutes.

2. The method of claim 1 wherein the step (d) catalyst is selected from the group consisting of alumina, titania, silica gel and mineral acids.

3. The method of claim 1 wherein the step (d) catalyst is $KHSO_4$.

4. The method of claim 1 wherein the step (d) reaction is conducted for a period of from about 0.2 minutes to about 2 minutes.

5. The method of claim 1 wherein the step (d) reaction is conducted at a vacuum of from about 0.5 mm HgA to about 250 mm HgA.

6. The method of claim 1 wherein the step (c) catalyst is Pd/C.

7. The method of claim 1 wherein the step (c) catalyst is Raney Nickel.

8. The method of claim 1 wherein the reaction step (c) is conducted until substantial completion of hydrogenation.

9. The method of claim 1 wherein the reaction step (c) is conducted at a pressure of from about 14.7 psig to about 5,000 psig.

10. A process for the production of 4-acetoxystyrene which comprises:

a) acylating phenol with acetic anhydride to produce 4-hydroxyacetophenone; and b) acylating the 4-hydroxyacetophenone with acetic anhydride to form 4-acetoxyacetophenone; and c) hydrogenating 4-acetoxyacetophenone with a suitable reagent, for a sufficient time to produce 4-acetoxyphenylmethylcarbinol; and d) heating 4-acetoxyphenylmethylcarbinol, in the presence of a catalytic amount of an acid catalyst, at a temperature of from about 85° C. to 300° C. under a pressure of from about 0.1 mm HgA to about 760 mm HgA for a period of time of from about 0.2 minutes to about 10 minutes.

11. The method of claim 10 wherein the step (d) catalyst is selected from the group consisting of alumina, titania, silica gel, mineral acids and $KHSO_4$.

12. The method of claim 10 wherein said step (c) reagent is selected from the group consisting of $NaBH_4$, lithium aluminum hydride, hydrogen and diisobutyl aluminum hydride.

* * * * *